United States Patent [19]

Reddy et al.

[11] Patent Number: 5,114,970

[45] Date of Patent: May 19, 1992

[54] USE OF 3-IODO-2-CHLORO-2-PROPENENITRILE AS AN ANTIMICROBIAL

[75] Inventors: Kalakota S. Reddy; Connie I. Deford, both of Midland, Mich.

[73] Assignee: The Dow Chemical Company, Midland, Mich.

[21] Appl. No.: 735,570

[22] Filed: Jul. 25, 1991

[51] Int. Cl.$^5$ .............................................. A01N 37/34
[52] U.S. Cl. ......................................... 514/526; 71/67; 162/161; 210/764
[58] Field of Search ........................... 514/526; 71/67; 162/161; 210/764

[56] References Cited

U.S. PATENT DOCUMENTS

| | | | |
|---|---|---|---|
| 2,433,742 | 12/1947 | Davis | 514/526 |
| 2,437,998 | 3/1948 | Clifford et al. | 260/464 |
| 2,455,689 | 12/1948 | Marple et al. | 260/465.9 |
| 3,361,786 | 1/1968 | Fink | 260/465.7 |
| 4,283,304 | 8/1981 | Bryant et al. | 252/413 |
| 4,294,777 | 10/1981 | Bockmann et al. | 260/544 |
| 5,039,702 | 8/1991 | Brandman et al. | 514/526 |

FOREIGN PATENT DOCUMENTS

89/07890  9/1989  World Int. Prop. O.

*Primary Examiner*—Allen J. Robinson

[57] ABSTRACT

The present invention is directed to a method of using a compound corresponding to the formula:

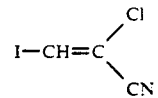

as an antimicrobial agent comprising contacting a microorganism or a habitat thereof with an antimicrobially effective amount of the compound. This 3-iodo-2-chloro-2-propenenitrile compound has been found to exhibit a high degree of antimicrobial activity in industrial and commercial applications and compositions containing this compound are so employed. An antimicrobial composition comprising and a process for the preparation of the 3-iodo-2-chloro-2-propenenitrile compound are also disclosed.

2 Claims, No Drawings

USE OF 3-IODO-2-CHLORO-2-PROPENENITRILE AS AN ANTIMICROBIAL

BACKGROUND OF THE INVENTION

The field of this invention is a method of using an iodo-substituted acrylonitrile compound as an antimicrobial.

Halogen substituted acrylonitrile compounds are well known and have been used for a variety of uses. For example, U.S. Pat. No. 2,433,742 discloses that halogen-substituted aorylonitrile compounds may be used to control insects, particularly by the fumigation of enclosed spaces.

U.S. Pat. No. 4,294,777 discloses a substituted compound of the formula:

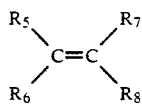

wherein $R_5$ to $R_8$ can be identical or different and represent hydrogen, nitrile, halogen or other substituents. These compounds are taught to be useful in a process for color stabilizing an aromatic carboxylic acid chloride.

PCT International Publication Number WO 89/07890, published Sep. 8, 1989, to Harold A. Brandman et al., discloses an α-halo-β-(substituted)thioacrylonitrile of the formula:

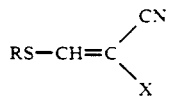

wherein X is a halogen and R is a lower alkyl, aryl, aralkyl, heterocyclo, or a thiocarbonyl group. This compound is taught to be useful as an effective antimicrobial agent.

The desirability of identifying or discovering new antimicrobial agents is widely recognized for several reasons. These reasons include the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

The present invention solves these problems by disclosing a compound which may be employed as an antimicrobial.

SUMMARY OF THE INVENTION

The present invention is directed to a method of using a compound corresponding to the formula:

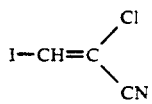

as an antimicrobial agent comprising contacting a microorganism or a habitat thereof with an antimicrobially effective amount of the compound.

The present invention also includes an antimicrobial composition comprising a liquid diluent and an antimicrobially effective amount of a compound corresponding to the formula:

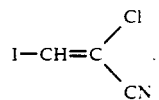

The present invention also includes a process for the preparation of a compound corresponding to the formula:

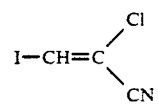

comprising contacting a compound corresponding to the formula:

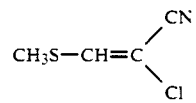

at reactive conditions with an effective amount of sodium periodate.

DETAILED DESCRIPTION OF THE INVENTION

The present invention is directed to a method of using a compound corresponding to the formula:

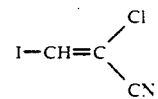

as an antimicrobial agent. This 3-iodo-2-chloro-2-propenenitrile compound is disclosed, for example, in U.S. Pat. Nos. 2,437,998 and 2,455,689.

The method of this invention is useful for inhibiting microorganisms, particularly bacteria, fungi, and algae, which comprises contacting said microorganisms or a habitat thereof with an antimicrobially effective amount of the compound.

As used herein, the term "antimicrobially effective amount" refers to that amount of the 3-iodo-2-chloro-2-propenenitrile compound needed to exhibit inhibition of selected organisms. Typically, this amount of the 3-iodo-2-chloro-2-propenenitrile compound is from about 10 parts per million (ppm) to about 5000 ppm by weight of a total habitat or solution. Preferably, this amount varies from about 100 ppm to about 1000 ppm by weight of a total habitat or solution.

As used herein, the term "habitat" refers to a place or type of site where a microorganism naturally or normally lives or grows. Typically, such a microorganism habitat will be an area that comprises a moisture, nutrient, and/or an oxygen source such as, for example, a cooling tower.

The 3-iodo-2-chloro-2-propenenitrile compound used herein is not active at the same concentration against different microbial species. That is, there is some species-to-species variation in antimicrobial potency and spectrum of antimicrobial activity. Also, the exact concentration of the 3-iodo-2-chloro-2-propenenitrile compound to be added in the treatment of industrial and consumer formulations may vary within a product type depending upon the components of the formulation. It is within the skill in the art to adjust the concentration of the antimicrobial agent to achieve the desired inhibition.

The terms "inhibition", "inhibit" or "inhibiting" refer to suppression, control, stasis, kill or any other interference with the normal life processes of microorganisms that is adverse to such microorganisms.

The 3-iodo-2-chloro-2-propenenitrile compound used in this invention is useful as an antimicrobial additive such as in an antimicrobial composition comprising a liquid diluent and an antimicrobially effective amount of the 3-iodo-2-chloro-2-propenenitrile compound. In such compositions, the 3-iodo-2-chloro-2-propenenitrile compound may be added as a concentrate or diluted with liquid to produce the ultimate treating composition, wherein the liquid could be water or an organic solvent such as glycols, alcohols, or acetone. A preferred liquid diluent is a glycol such as propylene glycol or tetraethylene glycol. The 3-iodo-2-chloro-2-propenenitrile compound may also be added alone or in combination with other preservatives.

The 3-iodo-2-chloro-2-propenenitrile compound used in this invention is useful as an antimicrobial additive to such industrial products as styrene-butadiene latexes used for paper coatings, paints, inks, adhesives, soaps, cutting oils, textiles, and paper and pigment slurries. The 3-iodo-2-chloro-2- propenenitrile compound is also useful as an antimicrobial additive in such personal care products as hand creams, lotions, shampoos, and hand soaps. A further advantage of this invention is its cost-effectiveness for applications which need to have an antimicrobial continuously replenished, such as in cooling towers and pulp and paper mills.

The 3-iodo-2-chloro-2-propenenitrile compound used in the present invention can be prepared by the reaction of a 2-chloro-3-methylthio-2-propenenitrile precursor with sodium periodate under reactive conditions. The general reaction scheme is as follows:

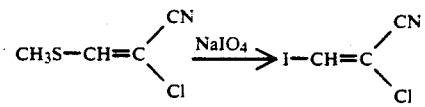

A preferred method of preparing the 3-iodo-2-chloro-2-propenenitrile compound is to dissolve 2-chloro-3-methylthio-2-propenenitrile in a mixture of water and an inert, water-miscible solvent such as tetrahydrofuran, dioxane, isopropanol, polyglycols and their ethers, or dimethylformamide. The concentration of the 2-chloro-3-methylthio-2-propenenitrile is not critical and conveniently is in the range from about 1.5 to about 2.0 moles. An effective amount of sodium periodate is then added to the solution.

In the present specification and claims, the term "effective amount" of the sodium periodate refers to that amount of sodium periodate needed to achieve the desired 3-iodo-2-chloro-2-propenenitrile compound. Such an amount will vary depending upon the amount of 3-iodo-2-chloro-2-propenenitrile compound desired as a recovered product and also upon the conditions at which the 3-iodo-2-chloro-2-propenenitrile compound is prepared. In carrying out this reaction, the 2-chloro-3-methylthio-2-propenenitrile precursor and the sodium periodate are typically mixed together in substantially equimolar amounts.

In the present specification and claims, the term "reactive conditions" is employed to designate the conditions under which the 2-chloro-3-methylthio-2-propenenitrile precursor is contacted with an effective amount of sodium periodate to allow for iodination of the precursor to produce the desired 3-iodo-2-chloro-2-propenenitrile compound. The reactive conditions should be such that the sodium periodate may be conveniently contacted with the 2-chloro-3-methylthio-2-propenenitrile precursor.

The reaction should preferably be run at atmospheric pressure. The reaction temperature should preferably be between $-20°$ C. and $50°$ C. The reaction temperature is most preferably kept below $10°$ C. for the time required for addition of the sodium periodate.

An alternative process for preparing the 3-iodo-2-chloro-2-propenenitrile compound used in the present invention is disclosed in U.S. Pat. No. 3,361,786. Synthesis of 2-Chloro-3-Methylthio-2-Propenenitrile Synthesis of 2- Chloro-3-Methylthio-2-Propenenitrile The synthesis of the 2-chloro-3-methylthio-2-propenenitrile precursor begins with the chlorination of acrylonitrile to form 2,2,3-trichloropropionitrile. This chlorination is straightforward and is described in the art, such as in N. C. Lorette, "The Addition of Chlorine to Acrylonitrile", *J. Org. Chem.*, Vol. 26, pp. 2324-2327, 1960. Overall yields of over 90 percent based on acrylonitrile are achievable.

Dehydrochlorination of 2,2,3-trichloropropionitrile yields an isomeric mixture of 2,3-dichloroacrylonitrile. This dehydrochlorination can be carried out by heating the 2,2,3-trichloropropionitrile in the presence of a catalyst. Purification of the 2,3-dichloroacrylonitrile prior to subsequent reaction is optional. This dehydrochlorination is straightforward and is described in the art, such as in U.S. Pat. Nos. 2,385,550 or 3,527,787.

The 2,3-dichloroacrylonitrile may be reacted with an alkaline earth metal salt of a methylsubstituted mercaptan to form the 2-chloro-3-methylthio-2-propenenitrile precursor in alkanols or aprotic solvents. The reaction temperature, stoichiometries, and mode of addition are important to obtain acceptable isolated yields (greater than 85 percent from 2,3-dichloroacrylonitrile). Such a process is described, for example, in PCT International Publication Number WO 89/07890.

The following examples illustrate the present invention and the manner by which it can be practiced but, as such, should not be construed as limitations upon the overall scope of the same.

EXAMPLE 1

Preparation Of 3-Iodo-2-Chloro-2-Propenenitrile

A solution of 3-methylthio-2-chloro-2- propenenitrile (5 g, 0.037 mole) in 50 ml of dioxane/water (3 1, by weight) is treated with small portions of sodium periodate (8.0 g, 0.037 mole) at room temperature. The reaction solution is heated at $60°$ C. for 4 hours and left at room temperature overnight. The solids are filtered and the filtrate is concentrated to half of its volume and then extracted twice with 100 ml portions of dichloromethane. The combined dichloromethane extracts are dried over anhydrous sodium sulfate, filtered and concentrated on a rotary evaporator to yield 4.8 g of crude product. A portion of the crude product (2.0 g) is purified by silica gel flash column chromatography to give 0.3 g of colorless heavy oil which is greater than 99.5 percent pure by gas chromatographic analysis (GC). The structure identity is confirmed by proton spectroscopy ($^1$H) and carbon nuclear magnetic resonance spectroscopy (NMR), infrared spectroscopy (IR) and gas chromatography/mass spectrometry (GC/MS).

Antimicrobial Activity

The 3-iodo-2-chloro-2-propenenitrile compound used in the present invention is useful because of its antimicrobial activity and can be used as an antibacterial and/or an antifungal agent. The 3-iodo-2-chloro-2-propenenitrile compound's effectiveness varies with the concentration of the compound used and the particular organisms to be controlled. The antimicrobial activity of the 3-iodo-2-chloro-2-propenenitrile compound is demonstrated by the following techniques.

The minimum inhibitory concentration (MIC) for the 3-iodo-2-chloro-2-propenenitrile compound is determined for 9 bacteria, using nutrient agar, and 7 yeast and fungi, using malt yeast agar. A one percent solution of the compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-tris-(hydroxymethyl)methyl-glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the compound is added (except in the controls where no compound is added) to the respective test tubes so that the final concentrations are 500, 250, 100, 50, 25, 10, 5, 2.5, 1.0 and zero parts per million of the compound in the agar, thus having a known concentration of compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table I lists the bacteria, yeast and fungi used in the MIC test described above along with their respeotive American Type Culture Collection (ATCC) identification numbers.

TABLE 1

Organisms used in the Minimum Inhibitory Concentration Test

| Organism | ATCC No. |
|---|---|
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables II and III, the MIC values of the 3-iodo-2-chloro-2-propenenitrile compound as compared to the MIC of a standard commercial preservative (DOWICIL TM 75, a trademark of The Dow Chemical Company, with 1-(3-chloroallyl)-3,5,7-triaza-1-azoniaadamantane chloride as the active agent) are set forth for the bacteria organisms and yeast/fungi organisms which are listed in Table I. As can be seen from Tables II and III, the 3-iodo-2-chloro-2-propenenitrile compound generally achieves better antimicrobial results than the standard oommeroial preservative. With such antimicrobial aotivity, the 3-iodo-2-chloro-2-propenenitrile compound should have the ability to serve as a preservative in a variety of formulated industrial, household, and commercial products such as latex, tape joint, hand lotion, and shampoo compositions.

TABLE II

Minimum Inhibitory Concentrations for Test Compounds in Bacteria Species (in ppm)

| Compound | ORGANISMS | | | | | | | | |
|---|---|---|---|---|---|---|---|---|---|
| | Bs | Ea | Ec | Kp | Pv | PRD | Pa | Sc | Sa |
| 3-iodo-2-chloro-2-propenenitrile | | | | | | | | | |
| pH 6.8 | 25 | 50 | 50 | 50 | 50 | 50 | 50 | 25 | 25 |
| pH 8.2 | 25 | 100 | 100 | 100 | 50 | 100 | 50 | 50 | 50 |
| DOWICIL ™ 75 | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |

TABLE III

Minimum Inhibitory Concentrations for Test Compounds in Yeast/Fungi Species (in ppm)

| COMPOUND | ORGANISMS | | | | | | |
|---|---|---|---|---|---|---|---|
| | An | Ca | Pc | Sc | Tv | Ap | Fo |
| 3-iodo-2-chloro-2-propenenitrile | <10 | <10 | <10 | <10 | 25 | <10 | <10 |
| DOWICIL ™ 75 | >500 | >500 | >500 | >500 | >500 | >500 | >500 |

What is claimed is:

1. A method for combatting fungi or bacteria which comprises contacting said fungi, bacteria or habitat thereof with a fungicidally or bactericidally effective amount of a compound of the formula:

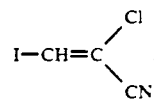

2. The method of claim 1 wherein the compound corresponding to the formula:

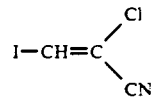

is used in an amount of from about 10 parts per million to about 5000 parts per million by weight of a total habitat.

* * * * *